United States Patent
Biresaw et al.

(10) Patent No.: US 11,370,745 B2
(45) Date of Patent: Jun. 28, 2022

(54) BIO-BASED BRANCHED ESTOLIDE COMPOUNDS

(71) Applicant: The United States of America, as represented by the Secretary of Agriculture, Washington, DC (US)

(72) Inventors: Girma Biresaw, Peoria, IL (US); Steven C. Cermak, Galesburg, IL (US); Helen N. Lew, Wynnewood, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/157,046

(22) Filed: Jan. 25, 2021

(65) Prior Publication Data
US 2021/0230097 A1 Jul. 29, 2021

Related U.S. Application Data

(60) Provisional application No. 62/967,296, filed on Jan. 29, 2020.

(51) Int. Cl.
*C07C 69/67* (2006.01)
*C07C 69/675* (2006.01)
*C10M 105/34* (2006.01)

(52) U.S. Cl.
CPC ............ *C07C 69/675* (2013.01); *C07C 69/67* (2013.01); *C10M 105/34* (2013.01)

(58) Field of Classification Search
CPC . C10M 105/34; C10M 2207/28; C07C 69/67; C07C 69/675
See application file for complete search history.

(56) References Cited

U.S. PATENT DOCUMENTS

| 6,018,063 A | 1/2000 | Isbell |
| 9,133,410 B2* | 9/2015 | Bredsguard .......... C10M 105/36 |
| 2013/0338050 A1* | 12/2013 | Bredsguard .......... C10M 169/04 |
| | | 508/465 |

FOREIGN PATENT DOCUMENTS

EP 0665286 B1 3/2000
WO 2017027388 A1 2/2017

OTHER PUBLICATIONS

Isbell, T., Chemistry and physical properties of estolides, Grasas Y Aceites, 62 (1), pp. 8-20 (Year: 2011).*
(Continued)

*Primary Examiner* — Yate' K Cutliff
(74) *Attorney, Agent, or Firm* — John Fado; Maria Restrepo-Hartwig

(57) ABSTRACT

A branched estolide compound of the formula:

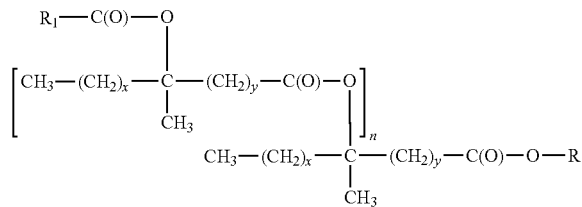

wherein x and y are equal to 1 or greater;
wherein x+y=14;
wherein n is 0, 1, or greater than 1;
wherein R is H or wherein R=C1 to C18 straight alcohols or C4 to C12 branched alcohols;
(Continued)

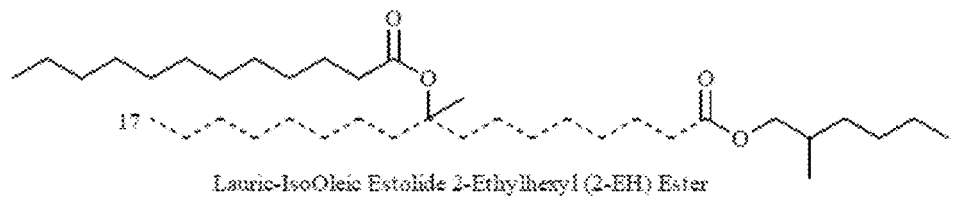

Lauric-IsoOleic Estolide 2-Ethylhexyl (2-EH) Ester

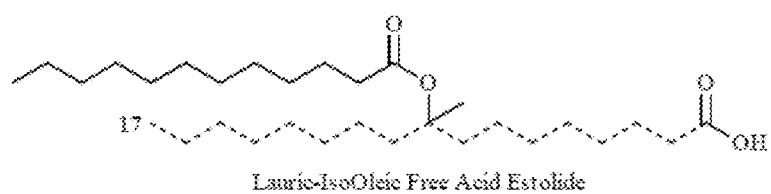

Lauric-IsoOleic Free Acid Estolide

Dashed lines indicate several possible positions for the branching methyl group and estolide linkage.

wherein $R_1$ is a residual fragment of octanoic, decanoic, lauric, coconut, myristic, palmitic, stearic, oleic, iso-stearic or iso-oleic acids.

9 Claims, 10 Drawing Sheets

(56) References Cited

OTHER PUBLICATIONS

Cermak, S.C. et al., "Synthesis and physical properties of new coco-oleic estolide branched esters", (2015) Industrial Crops and Products 74:171-177.
International Search Report dated May 13, 2021.

* cited by examiner

Oleic-Coco estolide FA

Oleic-oleic estolide 2-ethylhexyl esters

Oleic-coco estolide 2-ethylhexyl esters

Z-Iso-oleic Acid

E-Iso-oleic Acid

Dashed lines indicate several possible positions for the branching methyl group and estolide linkage.

The estolide position was distributed from positions 5–13 with the original Δ9 and Δ10 positions having the greatest abundances.

Fig. 7 Structures of C4 to C12 branched alcohols.
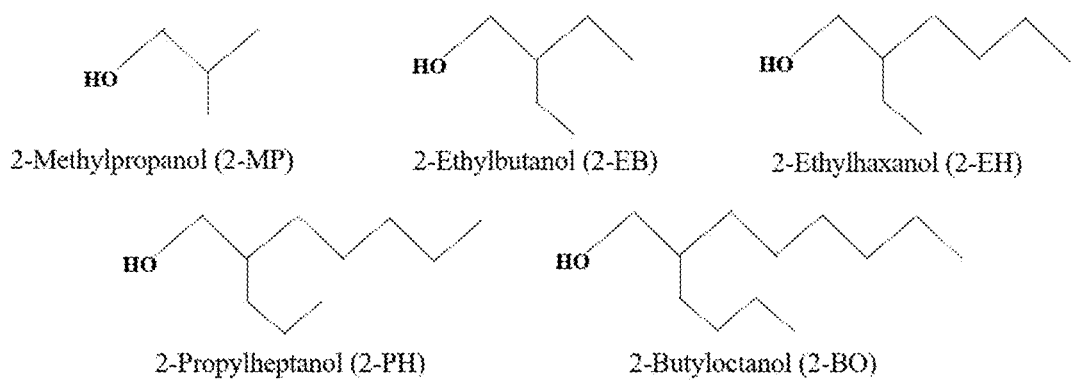
2-MP: C4 branched alcohol
2-EB: C6 branched alcohol
2-EH: C8 branched alcohol
2-PH; C10 branched alcohol
2-BO: C12 branched alcohol

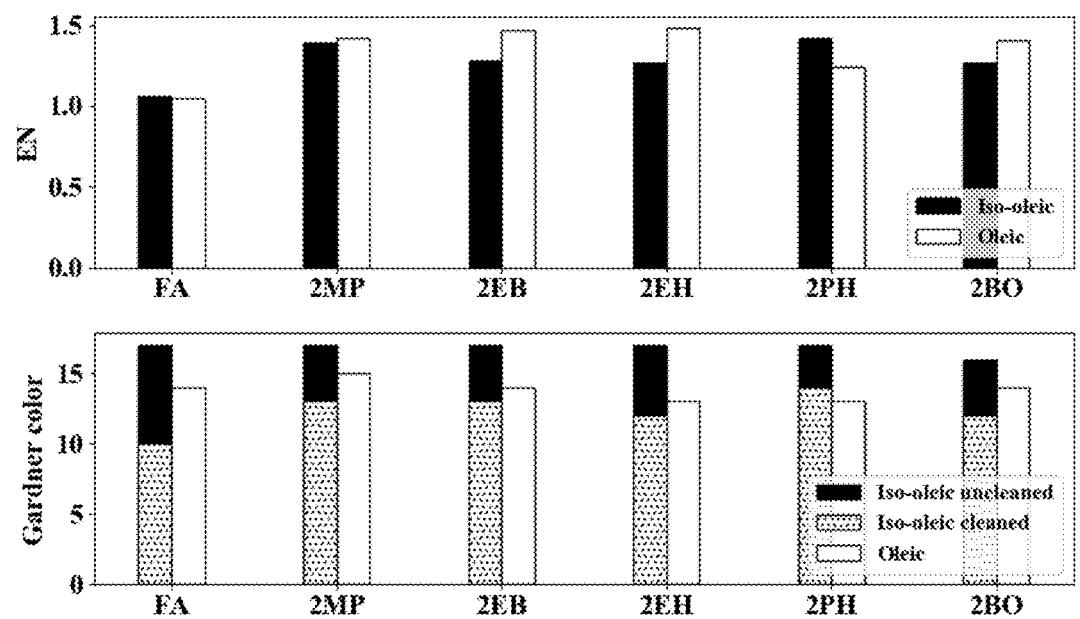
Fig. 8 Properties of iso-oleic- and oleic-coconut estolide free acids and esters
*FA-free acid Fig. 9 Viscosity and VI of iso-oleic- and oleic-coconut estolide free acids and esters
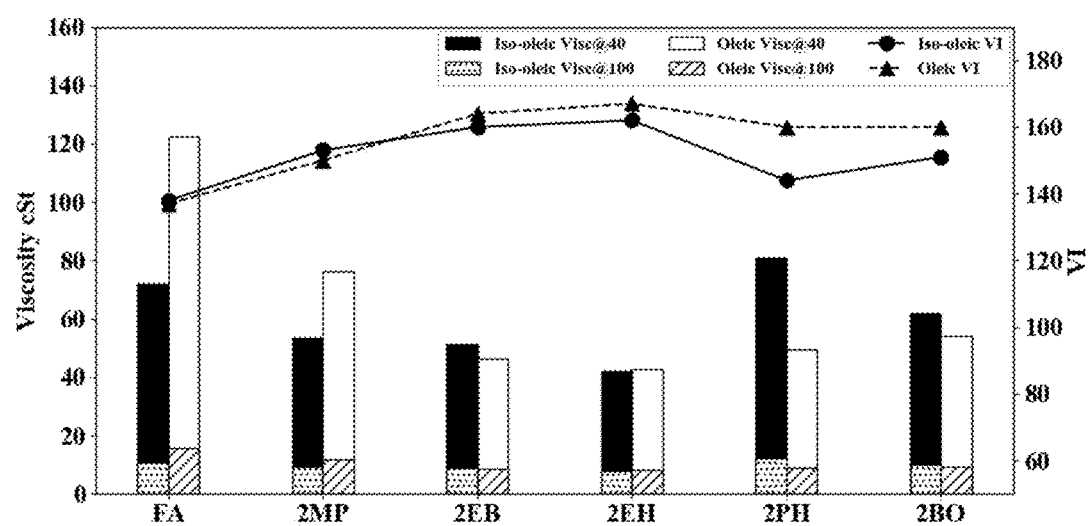

Fig. 10 Lower temperature properties and oxidation stability of iso-oleic- and oleic-coconut estolide free acid and esters
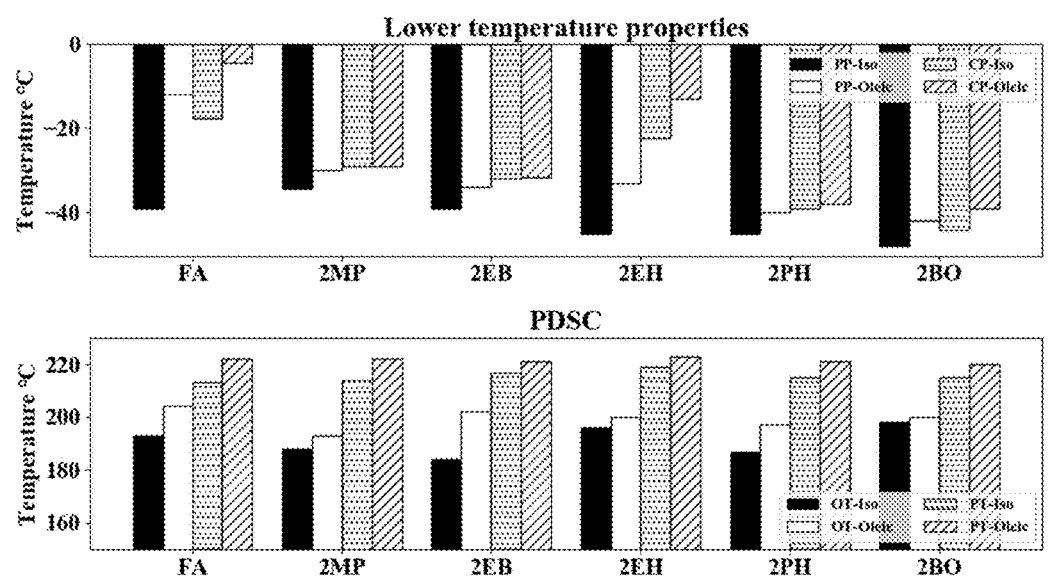

BIO-BASED BRANCHED ESTOLIDE COMPOUNDS

REFERENCE TO RELATED APPLICATION

This application claims the benefit of U.S. Provisional Application No. 62/967,296, filed 29 Jan. 2019, which is incorporated herein by reference in its entirety.

BACKGROUND OF THE INVENTION

Disclosed are branched estolide compounds of the formula:

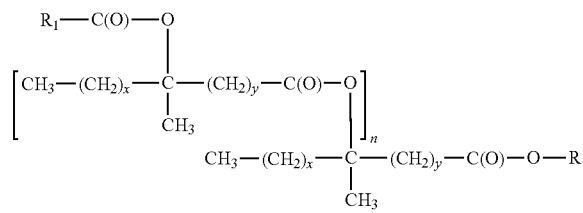

wherein x and y are equal to 1 or greater;
wherein x+y=14;
wherein n is 0, 1, or greater than 1;
wherein R is H or wherein R=C1 to C18 straight alcohols or C4 to C12 branched alcohols;
wherein $R_1$ is a residual fragment of octanoic, decanoic, lauric, coconut, myristic, palmitic, stearic, oleic, iso-stearic or iso-oleic acids.

Previously described estolides have the following formula:

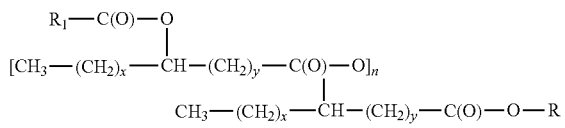

wherein x and y are equal to 1 or greater;
wherein x+y=15;
wherein n is 0, 1, or greater than 1;
wherein R is H or wherein R=C1 to C18 straight alcohols or C4 to C12 branched alcohols;
wherein $R_1$ is a residual fragment of octanoic, decanoic, lauric, coconut, myristic, palmitic, stearic, or oleic acid.

Estolides are biobased synthetic esters obtained from the reaction of a fatty acid with a double bond (e.g., oleic acid), hydroxy group (e.g., ricinoleic acid), or epoxide on its chain (see examples in FIG. 1), with a second fatty acid of similar or different structure, in the presence of a catalyst.

The reaction of the carboxylic acid of one fatty acid with the double bond, hydroxy group or epoxide group of the second fatty acid results in the formation of an ester linkage on the chain, and a free carboxylic acid at the end. Depending on the structures and relative compositions of the fatty acids used in the synthesis, further esterification can occur resulting in a complex mixture of oligomeric products. Products from such synthesis are called estolide free acids (FA). Examples of estolide free acid synthesis from homo-oligomerization of oleic acid and co-oligomerization of oleic acid with lauric acid is illustrated in FIG. 2.

Estolide FAs can be reacted further with appropriate alcohols to produce the estolide esters. The most widely used alcohol for such transformation is 2-ethyl hexanol (2-EH) which provides estolides with better cold flow properties than other alcohol structures. Structures of estolide 2-EH esters from homo-oligomerization of oleic (oleic-oleic), and co-oligomerization of oleic with lauric acid (oleic-coco) are shown in FIG. 3.

In general, estolide FAs display higher viscosity, higher pour point, higher cloud point, and lower VI than estolide esters. This is illustrated in FIG. 4 which compares the pour point of several co-oligomer oleic estolide FAs with the corresponding estolide esters as a function of the co-fatty acid chain length (Cermak, S. C., and T. A. Isbell, Industrial Crops and Products, 16: 119-127 (2002)).

The properties of estolide FAs depend on several synthetic parameter including, for example, the structure of the fatty acids, the ratio of fatty acids, the catalyst, reaction temperature, and reaction time. Examples of the effect of fatty acid ratio on estolide 2-EH ester properties have been reported (Cermak, S. C., and T. A. Isbell, Ind. Crops Products, 18: 183-196 (2003)).

Estolides to date have been synthesized from fatty acids, mostly derived from vegetable oils and fats, with no branching in the fatty acid structure in the base unit. The predominant such fatty acid used in estolide synthesis has been oleic acid. Recently, a process was developed for isomerizing oleic acid into iso-oleic acid (or methyl branched-chain fatty acid) (Ngo, H., et al., European J of Lipid Science and Technology, 115:676-683 (2013)), in which a methyl branch was introduced at the double bond. In addition, the double bond with the methyl branch is positioned at random locations on the chain. FIG. 5 shows the proposed structure of iso-oleic acid.

Herein we disclose iso-estolides (or branched estolides) made from iso-oleic acids having improved physical properties that make them more desirable and suitable as bio-based industrial or commercial products. The physical properties of the disclosed branched estolide compositions have surprisingly low pour points that are substantially lower than previously known estolide compounds and are superior to petroleum-based compounds designed for similar applications.

SUMMARY OF THE INVENTION

We have now discovered a family of novel branched estolide compounds derived from iso-oleic acids and certain organic acids which have unexpectedly low (superior) pour point temperatures. These branched estolide compounds are characterized by superior properties for use as lubricant base stocks. These branched estolides may also be used as lubricants without the need for fortifying additives normally required to improve the lubricating properties of base stocks.

The branched estolide compounds are generally characterized by the formula:

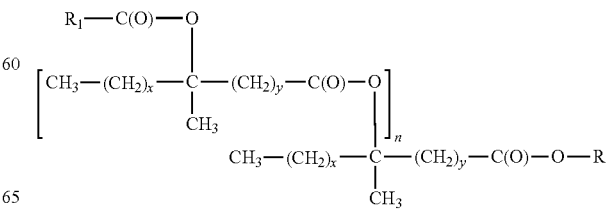

wherein x and y are equal to 1 or greater;
wherein x+y=14;
wherein n is 0, 1, or greater than 1;
wherein R is H or wherein R═C1 to C18 straight alcohols or C4 to C12 branched alcohols;
wherein $R_1$ is a residual fragment of octanoic, decanoic, lauric, coconut, myristic, palmitic, stearic, oleic, iso-stearic or iso-oleic acids.

It is an advantage of the invention to provide novel branched estolides and branched estolide esters having favorable physical properties as compared to commercially available industrial products such as soy-based fluids and petroleum-based fluids.

It is another advantage of the present invention to provide novel branched estolides and branched estolide esters that are cost effective to synthesize and exhibit desirable physical properties, such as pour and cloud points, viscosity, viscosity index, and other low temperature properties.

It is a further advantage of the present invention to provide a novel family of branched estolide compounds having superior properties for use as lubricant base stocks with reduced or eliminated use of undesirable additives.

An additional advantage of the invention is to provide novel materials with superior biodegradability and lubricating properties over petroleum-based and other similar commercially available products based on their low temperature properties.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

Exemplary

Exemplary

Exemplary

Exemplary

Exemplary

Exemplary

Exemplary FIG. 7 shows structures of C4 to C12 branched alcohols as described herein.

Exemplary FIG. 8 shows iso-oleic- and oleic-coconut estolide FA and C4 to C12 branched ester estolide numbers (EN) and gardner color as described herein.

Exemplary FIG. 9 shows iso-oleic- and oleic-coconut estolide FA and C4 to C12 branched esters viscosity and VI as described herein.

Exemplary FIG. 10 shows iso-oleic- and oleic-coconut estolide FA and C4 to C12 branched ester low temperature properties and oxidation stability as described herein.

DETAILED DESCRIPTION OF THE INVENTION

Disclosed are branched estolide compounds of the formula:

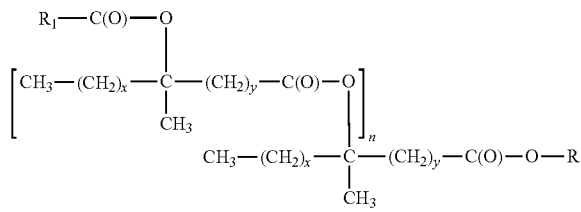

wherein x and y are equal to 1 or greater;
wherein x+y=14;
wherein n is 0, 1, or greater than 1;
wherein R is H or wherein R═C1 to C18 straight alcohols or C4 to C12 branched alcohols;
wherein $R_1$ is a residual fragment of octanoic, decanoic, lauric, coconut, myristic, palmitic, stearic, oleic, iso-stearic or iso-oleic acids.

"Residual Fragment" refers to at least one acyl moiety which is typical in compositions of the oil of reference and the acyl moiety could contain estolide(s).

"Branched alcohol" means that the "branch" is an alkyl group or a OH. For example, for 2-ethyl hexanol the "branch" is an ethyl group on the C6 chain (FIG. 7).

Figure 1:
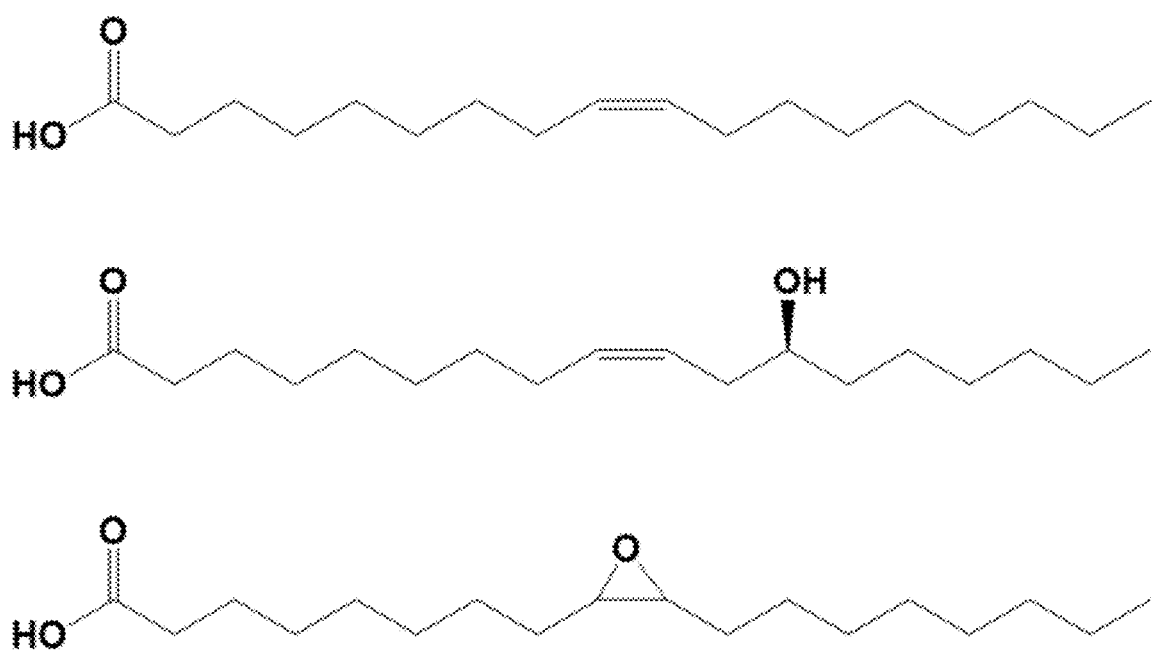
FIG. 1 shows examples of essential fatty acids structures for estolide synthesis as described herein.
Figure 2:
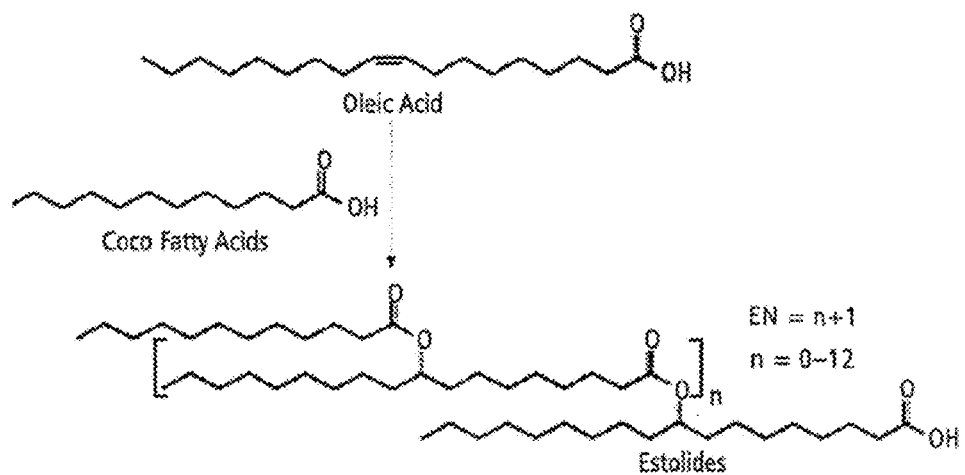
FIG. 2 shows schematics of estolide synthesis as described herein.
Figure 3:
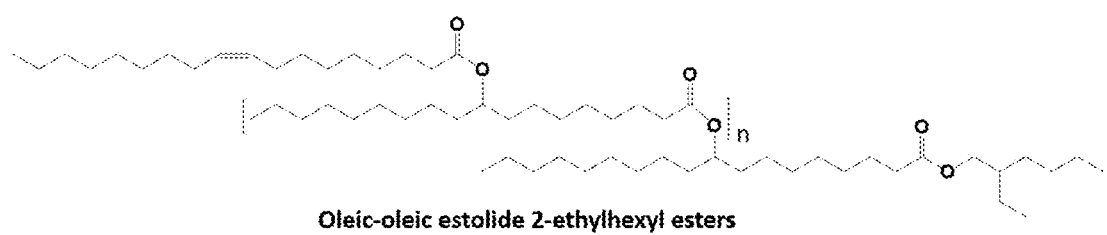
FIG. 3 shows structures of estolide 2-EH esters as described herein.
Figure 3:
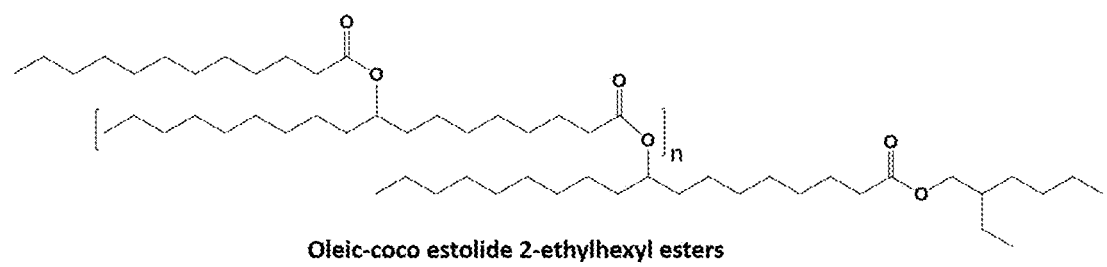
Figure 4:
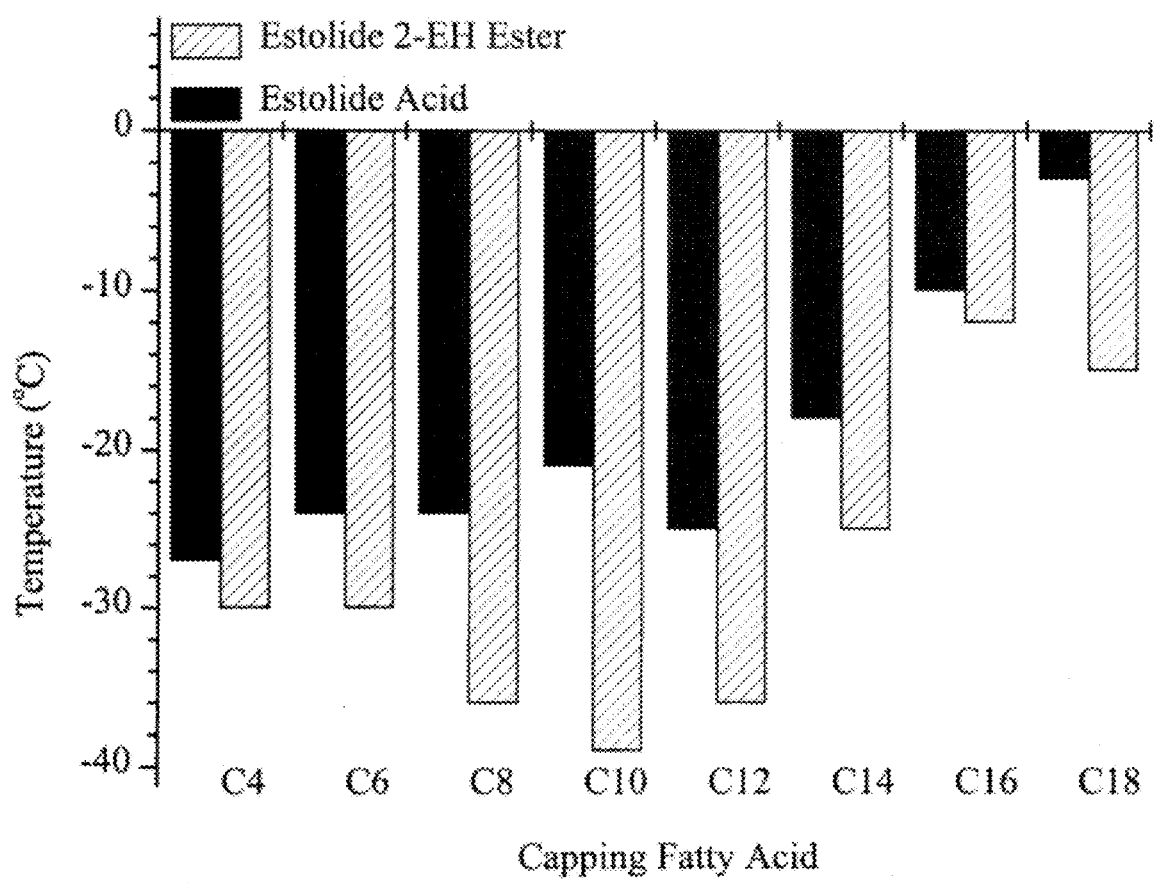
FIG. 4 shows pour point of estolide FA vs. corresponding estolide 2-EH esters (Cermak, S. C., and T. A. Isbell, Industrial Crops and Products, 16: 119-127 (2002)) as described herein.
Figure 5:
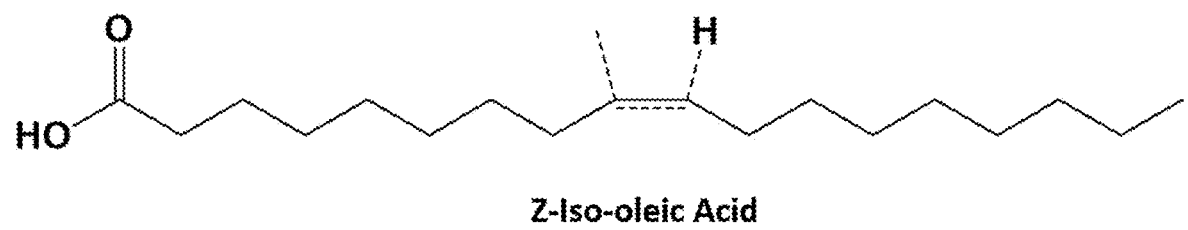
FIG. 5 shows proposed structures of iso-oleic acid (Ngo et al., European J of Lipid Science and Technology, 115: 676-683 (2013)) as described herein.
Figure 5:
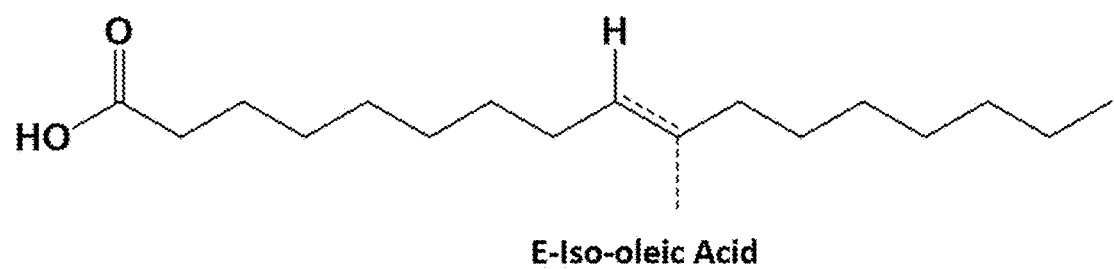
Figure 6A:
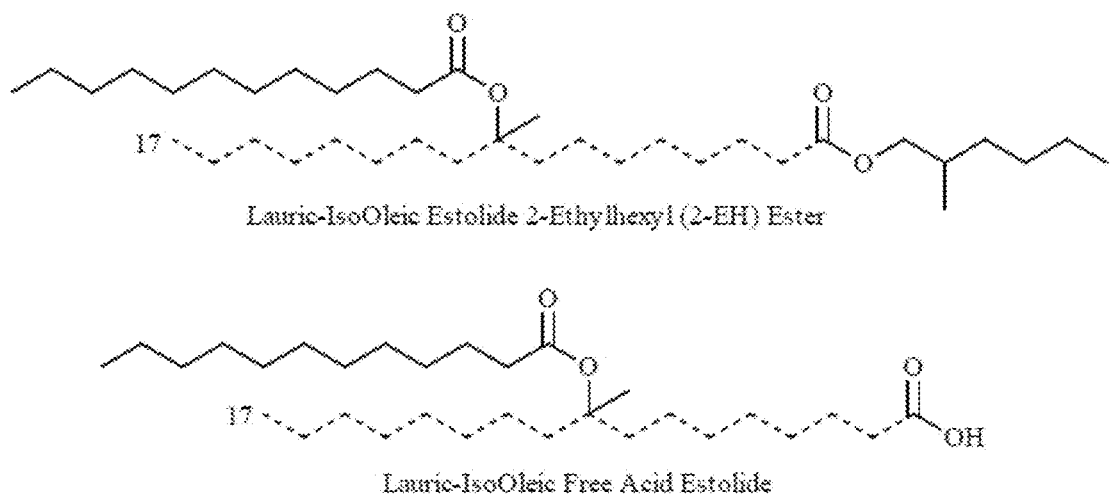
FIG. 6A shows proposed structures of lauric-iso-oleic FA and 2-EH ester branched estolides and Exemplary
Figure 6B:
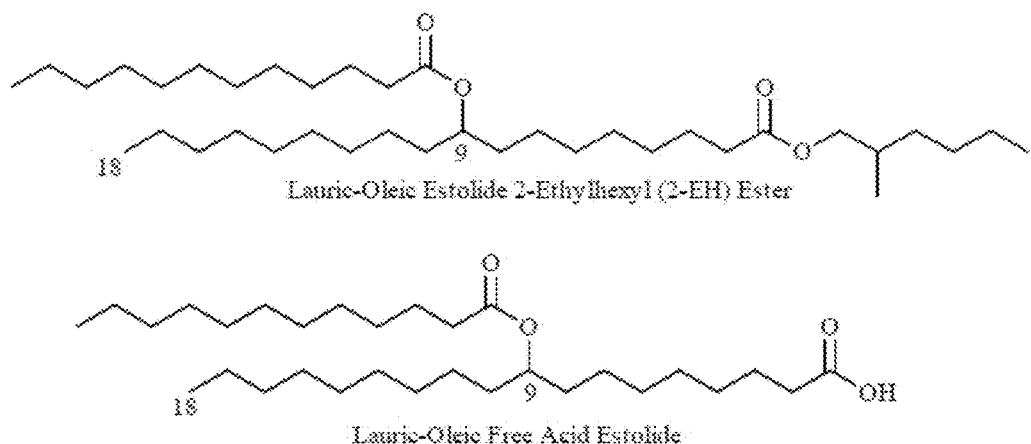
FIG. 6B shows proposed structures of lauric-oleic FA and 2-EH ester estolides as described herein.

The production of estolides by various routes is known in the art (e.g., JAOCS, 71(1): 169-174 1994); Erhan et al., JAOCS, 74(3): 249-254 (1997); Isbell et al., JAOCS, 74(4): 473-476 (1997); U.S. Pat. Nos. 6,018,063 & 6,316,649). Herein, branched estolide FAs and branched estolide 2-EH esters were synthesized by reacting iso-oleic acid (designated as Fatty Acid 1, FA 1, in subsequent Tables) with itself, or with a series of other fatty acids (designated as Fatty Acid 2, FA 2, in subsequent Tables), in the presence of a catalyst (e.g., $HClO_4$). A similar synthesis, under almost identical conditions, was also conducted by substituting oleic acid for iso-oleic acid. Details about the fatty acids, 2-ethylhexanol, $HClO_4$ and other key reagents used in the synthesis are summarized in Table 1. Schematics showing the structures of FA and 2-EH ester branched estolides from iso-oleic and oleic are illustrated in FIG. 6.

Examples of catalysts which may be used in the synthesis of the branched estolide compounds include strong mineral acids (e.g., $H_2SO_4$), super acids or Brønsted-Lowry acids (e.g., $HClO_4$), and Lewis acids (e.g., $BF_3$). Polymerization catalyst(s) include, for example, $Sn(Oct)_2$, $HClO_4$, and $H_2SO_4$, A particular advantage of the disclosed branched estolide compounds is their surprisingly low pour point. Comparable materials exhibit substantially higher pour points than the compounds of the invention. The disclosed branched estolide compounds are characterized by the following physical properties: for branched estolide esters, pour point in a range from about −60° C. (e.g., −60° C.) to about −18° C. (e.g., −18° C.), cloud point in a range from about −43° C. (e.g., −43° C.) to about −10° C. (e.g., −10° C.), viscosity at 40° C. in a range from about 41 cSt (e.g., 41 cSt) to about 87 cSt (e.g., 87 cSt), viscosity at 100° C. in a range from about 7 cSt (e.g., 7 cSt) to about 14 cSt (e.g., 14 cSt), and viscosity index in a range from at least about 152 (e.g., 152) to about 173 (e.g., 173); and for branched estolide free acids, pour point in a range from about −39° C. (e.g., −39° C.) to about −3° C. (e.g., −3° C.), cloud point in a range from about −64° C. (e.g., −64° C.) to 0° C., viscosity at 40° C. in a range from about 71 cSt (e.g., 71 cSt) to about 893 cSt (e.g., 893 cSt), viscosity at 100° C. in a range from about 20 cSt (e.g., 20 cSt) to about 56 cSt (e.g., 56 cSt), and viscosity index in a range from at least about 116 (e.g., 116) to about 139 (e.g., 139).

In embodiments, when used as a base stock, the disclosed branched estolide compounds can be admixed with an effective amount of other lubricating agents such as mineral or vegetable oils, other estolides, poly alpha olefins, polyol esters, oleates, diesters, conventional additive packages, bio-based additive packages, other natural or synthetic fluids, the like, and combinations thereof.

According to alternative embodiments, various additives are used in combination with the disclosed branched estolide compounds. In certain cases, as determined by a skilled artisan additives, though not preferred, may aid, for example, in addressing contamination, preventing premature breakdown, or increasing protective properties. In most cases where additives are desired, the compositions of the invention generally require small amounts of additives as compared to conventional fluids.

Examples of such additives include detergents, corrosion inhibitors, antioxidants, viscosity modifiers, friction modifiers, pour point depressants, dispersants, anti-foam agents, anti-misting agents, wax crystal modifiers/dewaxing aids, colorants, the like, and combinations thereof.

Other compounds (e.g., detergents known in the art) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising a detergent" means that the composition may or may not contain a detergent and that this description includes compositions that contain and do not contain a detergent. Also, by example, the phrase "optionally adding a detergent" means that the method may or may not involve adding a detergent and that this description includes methods that involve and do not involve adding a detergent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed, and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount. For example, about 1.0 g means 0.9 g to 1.1 g and all values within that range, whether specifically stated or not.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials: Iso-oleic acid product mixtures (78-89% iso-oleic) were synthesized as described below. Materials used in iso-oleic acid synthesis include: oleic acid (91 wt. % 18:1, 6.1 wt. % 18:2, 2.7 wt. % 18:0) from Aldrich Chemical (Milwaukee, Wis.); triphenylphosphine (99% pure) from Aldrich Chemical (Milwaukee, Wis.); and ammonium ferrierite zeolite (CP914C, $SiO_2/Al_2O_3$=20) from Zeolyst International Co. (Conshohocken, Pa.). The sources and purity of other fatty acids, C4 to C12 branched alcohols, $HClO_4$, and other chemicals used in synthesis and purification are listed in Table 1. Methanol, hexanes, and ethyl acetate were purchased from EMD Millipore Co. (Billerica, Mass.). Ethanol was purchased from AAPER Alcohol and Chemical Company (Shelbyville, Ky.). Sulfuric acid was purchased from LabChem Inc. (Zelienople, Pa.). Charcoal powder (−100 Particle size (mesh)) used for decolorizing estolide products were obtained from Sigma Aldrich (Milwaukee, Wis.). Silica powder (technical grade, pore size 60 Å, 230-400 mesh) used for filtering the charcoal powder from the decolorized solution was obtained from Sigma Aldrich (Milwaukee, Wis.). Filter paper was obtained from Whatman (Clifton, N.J.). Standard mixtures of fatty acid methyl esters (FAMEs) used in chromatography were obtained from Nu-Check Prep (Elysian, Minn.). All solvents used for chromatography and extraction were HPLC grade or equivalent and were used without further purification.

Gas Chromatography (GC): Hewlett-Packard 6890N Series gas chromatograph (Palo Alto, Calif.) equipped with a flame-ionization detector and an autosampler/injector was used for GC analysis. Analyses were conducted on a SP-2380 30 m×0.25 mm i.d. column (Supelco, Bellefonte, Pa.). Saturated C8-C30 FAMEs provided standards for making fatty acid and by-product assignments. Analysis were conducted as follows: column flow 1.0 mL/min with a helium head pressure of 15 psi; split ratio 50:1; programmed ramp 120 to 135° C. at 20° C./min, 135 to 265° C. at 7° C./min, hold 5 min at 265° C.; injector and detector temperatures set at 250° C. Saturated $C_8$-$C_{30}$ FAME provided standards were used to make FAME assignments.

Nuclear Magnetic Resonance (NMR): $^1H$ and $^{13}C$ nuclear magnetic resonance (NMR) spectra were obtained in CDCl3 on a Bruker Avance 500 NMR spectrometer (Bruker Corporation, Billerica, Mass.) using a 5-mm BBO probe operating at 500 MHz for 1H NMR and 126 MHz for 13C NMR. Chemical shifts are reported in parts per million (ppm) from tetramethylsilane calculated from the lock signal.

Estolide Numbers (EN): Estolide numbers (EN) were determined by GC from the SP-2380 column analysis as described before (Isbell, T. A., and R. Kleiman, Journal of the American Oil Chemists' Society, 71: 379-383 (1994)).

Gardner Color: Gardner color measurements were conducted on a Lovibond 3-Field Comparator from Tintometer Ltd. (Salisbury, England) using AOCS Method Td 1a-64 Gardner Color (1963).

Density, Viscosity and Viscosity Index (VI): Density, dynamic and kinematic viscosity as a function of temperature were obtained from measurements on a Stabinger SVM3000/G2 viscometer (Anton Paar GmbH, Graz, Austria) according to ASTM D7042-11a ("Standard test method for dynamic viscosity and density of liquids by Stabinger viscometer (and the Calculation of Kinematic Viscosity)," Annual Book of ASTM Standards, American Society for Testing and Materials: West Conshohocken, Pa., 05.04, 186-193 (2012)). Viscosity index (VI) was calculated from measured kinematic viscosity values at 40 and 100° C., in accordance with ASTM D2270-93 ("Standard practice for calculating viscosity index from kinematic viscosity at 40 and 100° C.," Annual Book of ASTM Standards, American Society for Testing and Materials: West Conshohocken, Pa., 05.01, 849-854 (2012)).

Pour Point (PP): Pour point was measured according to ASTM D97 ("Standard test method for pour point of petroleum products," Annual Book of ASTM Standards, American Society for Testing and Materials: West Conshohocken, Pa., 05.01, 100-104 (2012)) on a Lawler Model DR-4-20L automated pour point analyzer (Lawler Manufacturing Corp., Edison, N.J.).

Cloud Point (CP): Cloud point was measured according to ASTM D2500 ("Standard test method for cloud point of petroleum products," Annual Book of ASTM Standards, American Society for Testing and Materials: West Conshohocken, Pa., 05.01, 949-9532012 (2012)) on a Lawler Model DR-4-10L automated cloud point analyzer (Lawler Manufacturing Corp., Edison, N.J.).

Oxidation Stability—Onset (OT) and Peak (PT) Oxidation Temperatures: Onset (OT) and peak (PT) oxidation temperatures were measured on a Q20P pressurized differential scanning calorimeter (PDSC, TA Instruments—Waters LLC, New Castle, Del.) in accordance with ASTM D6186-08 ("Standard test method for oxidation induction time of lubricating oils by pressure differential scanning calorimetry (PDSC)," Annual Book of ASTM Standards, American Society for Testing and Materials: West Conshohocken, Pa., 05.03, 52-56 (2012)).

Total Acid Number (TAN): Acid value was measured on 751 GPD Titrino instrument (Metrohm Ltd., Herisau, Switzerland) following the official AOCS Method Te 2a-64 Acid Value (1963), with ethanol substituted for methanol to increase the solubility of the estolide esters during titration. All acid values were conducted in duplicate and average values are reported.

General Procedure for iso-Oleic Acid Synthesis: Nine reactions (one at 700 g and eight at 400 g scale) were conducted. In a typical reaction, 400 g of oleic acid was combined with 1.52 g triphenylphosphine (7.6 wt % to zeolite), 8 mL distilled water (40 wt % to zeolite) and 20 g solid zeolite Ferrierite catalyst (5 wt % to oleic acid; zeolite was calcined 5 h at 500° C., then stored at room temperature), in a mechanically stirred 600 mL pressure reactor (Parr Instruments, Moline, Ill.). The vessel was sealed, sparged with nitrogen, and brought to 260° C. The reactor was held at 260° C. for 48 h. The heat was turned off and the vessel left to cool to room temperature. The reaction mixture was passed over a 10 μm Ertel-Alsop filter with 18-20 psi nitrogen. The reactor was rinsed well with ethyl acetate, which was also filtered over the 10 μm Ertel-Alsop filter, but was kept separate from the neat reaction mixture. Solvent was removed from this latter fraction by rotary evaporation, and then the solvent-free filtered crude reaction mixtures were pooled Removal of saturated fatty acids and dimers from crude iso-oleic acid. Crude iso-oleic acid was mixed with an equal weight of ice-cold acetone and incubated for 20 h at −13° C. The material was filtered over Whatman #1 paper using a 1000 mL of cold acetone. The liquid was recrystallized a second time under the same conditions. Acetone was removed by rotary evaporation to isolate the crude iso-oleic acid. Dimers were removed from the twice recrystallized liquid via wiped film evaporation (VTA, Germany) with the addition funnel jacket at 60° C., the evaporator at 120-160° C., condenser at 25° C. and vacuum pressure at 0.05-0.1 mbar. Feed rate was 3 seconds per drop, and the wiper rotated at 300 rpm.

General Procedure for Branched Estolide Free Acid (FA) Synthesis: A general procedure is given here. Detailed quantities of reactants, reaction temperature, reaction time and yield for each specific branched estolide FA product is given in Table 2. An acid-catalyzed condensation reaction was conducted without solvent in a 1000 mL round bottom flask that had been pre-treated with an acidic wash. The proper quantities of fatty acid 1 (FA 1, Oleic acid or Iso-Oleic acid) and fatty acid 2 (FA 2, octanoic acid, etc; also known as capping fatty acids) were combined and heated at the selected temperature (60-70±0.1° C.) under house vacuum (7.5-10.9 kPa), and stirred with a Teflon coated stir bar. Once the desired temperature was reached, the selected amount of perchloric acid (0.04-0.10 equiv. relative to total fatty acids) was added, vacuum restored, and stirred at the selected temperature for 24-48 hrs. The solution was then allowed to cool to room temperature with stirring and quenched by the addition of aq. KOH (1.15 eq based on HClO4) in 90% ethanol/water solution and allowed to stir for at least 30 min. After warming, the sample was dissolved in hexane and then the pH of the solution adjusted to 5.0 to 6.0 using a pH 5 buffer (Aq. $NaH_2PO_4$). The organic layer was then washed with saturated NaCl solution, dried over anhydrous sodium sulfate, and filtered with Whatman #54 filter paper. All reactions were concentrated in vacuo and then Kugelrohr-distilled at 180-200° C. and 0.013-0.067 kPa to remove unreacted fatty acids and other by-products. The final product was then filtered with Whatman #54 filter paper, weighed for yield calculation.

General Procedure for Branched Estolide Ester Synthesis: A general procedure is given here. Detailed quantities of reactants, reaction temperature, reaction time and yield for each specific Branched Estolide ester product is given in Tables 3 and 4. An acid-catalyzed condensation reaction was conducted without solvent in a 1000 mL round bottom flask that had been pre-treated with an acidic wash. The proper quantities of fatty acid 1 (FA 1, Oleic acid or Iso-Oleic acid) and fatty acid 2 (FA 2, octanoic acid, etc.) were combined and heated at the selected temperature (60-70±0.1° C.) under house vacuum (7.5-10.9 kPa), and stirred with a Teflon coated stir bar. Once the desired temperature was reached, the required amount of perchloric acid (0.04-0.10 eq. relative to total fatty acids) was added, vacuum restored, and stirred for 24-48 hrs. Then, the required amount of alcohol was added to the vessel, vacuum restored, and the mixture stirred for an additional 6 h. After cooling, the reaction mixture was quenched by the addition of aq. KOH (1.15 eq based on $HClO_4$) in 90% ethanol/water solution and stirred for 30 min. The mixture was then dissolved in hexane and the pH adjusted to 5.0-6.0 using a pH 5 buffer (aq, $NaH_2PO_4$). The organic layer was then washed with a saturated NaCl solution, dried over anhydrous sodium sulfate, and filtered with Whatman #54 filter paper. The solution was then concentrated in vacuo and Kugelrohr-distilled at 180-200° C. and 0.013-0.067 kPa to remove unreacted alcohol, fatty acid/esters and non-estolide by-products. The final product was filtered with Whatman #54 filter paper and weighed to determine product yield.

Data analysis: Data analysis was conducted using IgorPro Version 5.0.3.0 software (WaveMetrics, Inc., Lake Oswego, Oreg.).

Key details about the synthesis parameters (concentrations, time, temperature, etc.) for the branched estolide FAs and branched estolide esters are provided in Tables 2, 3 and 4. Details about the synthesis and analytical procedures are given in below. Also shown in Tables 2, 3 and 4 are product yields and some pertinent properties of the branched estolide FA and branched estolide ester products.

As shown in Tables 1 and 2, the reaction time and amount of catalyst for some of the synthesis with iso-oleic acid were increased relative to those with oleic acid in order to increase the product yield. Herein, yield (%) is expressed relative to a theoretical maximum estolide product with estolide number of 1 (EN=1). The modified procedure had no effect on the degree of polymerization or EN but was able to increase product yield to values that were still below the yield from oleic acid. Also, the product mixtures from reaction of iso-oleic acid with coconut fatty acids were generally too dark (high Gardner Color) for cloud point evaluation and were subjected to further purification with charcoal powder (Tables 1 and 2), which gave lower yield but improved Gardner values.

Charcoal purification was conducted as follows: A sample of 50-100 g of branched estolide was dissolved in 300 mL of ethyl acetate to which 20 g of charcoal was added, the mixture swirled for about 10 s, let stand for 30 min and filtered on a Buchner funnel with filter paper containing a thick layer of silica powder on top. This process is repeated two more times after which the Buchner funnel was rinsed with excess ethyl acetate and the used filter paper and silica powder discarded. A new filter paper and silica powder were then placed in the funnel and the charcoal purification process repeated. The purified product was obtained after the ethyl acetate is removed by rotovap under house vacuum (20 mm Hg).

In general, branched estolides from iso-oleic acid and oleic acid gave comparable EN, TAN and GC. The branched estolide 2-EH esters (Table 3) from both oleic acid and iso-oleic acid displayed much lower TAN than the branched estolide FAs (Table 2).

Since the addition of the 2-EH alcohol to the branched estolide FA surprisingly provided superior properties to the product, other branched alcohols were examined to see if similar effects could be obtained. FIG. 7 shows the structures of C4 to C12 branched alcohols (2-methylpropanol (2-MP, C4), 2-ethylbutanol (2-EB, C6), 2-ethylhexanol (2-EH, C8), 2-propylheptanol (2-PH, C10) and 2-butyloctanol (2-no, C12)) used in the esterification of the estolides prepared from FA 1 and FA 2. Similar to Tables 1 & 2, key details about the synthesis parameters (concentrations, time, temperature, etc.) for these branched estolide esters are shown in Table 4. The reaction time and amount of catalyst for some of the synthesis with iso-oleic acid were also increased relative to those with oleic acid in order to increase the product yield. Herein, yield (%) is expressed relative to a theoretical maximum estolide product with estolide number of 1 (EN=1). The modified procedure had no effect on the degree of polymerization or EN but was able to increase product yield to values that were still below the yield from oleic acid. Also, the product mixtures from reaction of iso-oleic acid with coconut fatty acids were generally too dark (high Gardner Color) for cloud point evaluation and were subjected to further purification with charcoal powder (FIG. 8), which gave lower yield but improved Gardner values.

Branched Estolide Free Acid Properties: The viscosity and viscosity index (VI) of estolide free acids from iso-oleic acid vs. oleic acid are compared in Table 5. Listed in the first column of Table 5 and subsequent tables are the fatty acids (FA 2) used in the synthesis of estolides with oleic acid or iso-oleic acid (FA 1). The data in Table 5 indicates that iso-estolide FAs (branched estolide free acids from iso-oleic acid), were generally more viscous than estolide FAs (estolide free acids from oleic acid) at 400 and 100° C. The exceptions to this trend were lauric and coco, which displayed the reverse trend of higher viscosity for estolide FAs than those for branched estolide FAs. The branched estolide FAs gave wider kinematic viscosity range of 72-892 and 11-56 cSt, at 40° and 100° C., respectively, vs. 122-315 and 16-33 cSt. for estolide FAs at the corresponding temperatures. The VI data shows slightly higher VI for estolide FAs over those branched estolide FAs, with the exception of coco which showed higher VI for branched estolide FAs over that for estolide FA. One way of comparing the viscosity data in Table 5 is based on the size of the viscosity range at 40° and 100° C. A wider range is preferred because it allows for application on a wider range of lubricant viscosity grades. Based on this criteria, the iso-estolide will be preferred over the estolide. On the other hand, the viscosity ranges for the two products do not overlap and can be considered complimentary; with the estolides being applied for low viscosity grade products and the iso-estolide for higher grade products. However, if one needs to choose between the two then the iso-estolide will be preferred. It is not obvious how the methyl substitution in iso-estolides is related to its surprisingly wider viscosity range at 400 and 100° C.

Table 6 compares the pour point (PP) and cloud point (CP) of estolide vs. iso-estolide FAs. The data shows lower PP and CP for iso-estolides FAs than for estolides FAs. The exceptions were PP and CP for octanoic acid and PP for decanoic acid, where the reverse trend was observed. The fact that none of the iso-estolides displayed PP and CP above freezing whereas at least one estolide product did show such properties could be an indication of the surprisingly strong influence of the methyl branch in iso-estolides at disrupting crystallization of the oil during cooling.

Table 7 compares the onset (OT) and peak (PT) oxidation temperatures of estolide vs. iso-estolide FAs. The data shows higher OT and PT for most estolides FAs than for iso-estolides FAs. The exceptions were palmitic and stearic acids, which gave higher OT and PT for iso-estolide FAs than for estolides FAs. Estolides vs. iso-estolides displayed overlapping ranges of OT (169-204 vs 155-193° C.) and PT (189-222 vs. 179-222° C.), which can be used to infer that they have similar oxidation stability. The data supports such conclusion since OT/PT data are higher for some estolides but lower for others. Surprisingly it appears that the presence of random methyl branching did not improve or degrade the oxidation stability of iso-estolides. Estolide 2-Ethylhexyl (2-EH) Ester Properties: The kinematic viscosity of oleic vs. iso-oleic estolide 2-EH esters are compared in Table 8. The kinematic viscosity values for both types of estolide 2-EH esters, at 40° and 100° C., were considerably lower than those for the corresponding estolide FAs. Thus, the kinematic viscosity ranges for estolide 2-EH esters were 32-94 and 16-33 cSt, vs. 41-87 and 8-13 cSt. for iso-estolide 2-EH esters, at 40° and 100° C. At 40° C., most of the iso-estolide 2-EH esters displayed higher or similar kinematic viscosity relative to estolide 2-EH esters. The exceptions were 2-EH esters from octanoic and oleic acids which displayed the reverse trend. However, at 100° C., surprisingly estolide 2-EH esters consistently displayed higher kinematic viscosity than iso-estolides 2-EH esters. The estolide 2-EH esters also displayed slightly higher VI than iso-estolides 2-EH esters, which correlates well with their higher kinematic viscosity at 100° C. The fact that the 2-EH esters displayed lower viscosity than the free acids is a well-known and expected phenomenon in estolides, and is attributed to the absence of H-bonding after esterification of the free acid. The fact that the VI of the 2-EH esters of both estolides were higher than the corresponding free acid estolides is also a well-known result in estolide chemistry; but the reason for the higher VI of 2-EH esters is not understood.

Unlike the free acids, the 2-EH esters displayed overlapping range of kinematic viscosity at 40° C. (but not at 100° C.), which can be used to conclude no difference in kinematic viscosity at 40° C. This is consistent with the data in Table 8 which shows higher kinematic viscosity at 40° C. for some iso-estolides and the reverse for others. At 100° C., estolide 2-EH esters displayed higher kinematic viscosity range than iso-estolide, which correlates well with the higher VI range for estolide than for iso-estolide 2-EH esters. It is hard to explain the role of the methyl branch for the surprising difference in the kinematic viscosity range at 40 vs. 100° C. or for the difference in VI range of iso-estolides relative to estolides. It should be noted that the VI ranges are comparable to the API standard for PAO.

The pour point (PP) and cloud point (CP) of oleic vs. iso-oleic estolide 2-EH esters are compared in Table 9. The data shows consistently lower PP and CP values for iso-estolide 2-EH esters compared to those for oleic estolide 2-EH esters. There were a very small number of CP exceptions, where the CP values for iso-oleic estolide 2-EH were not lower but similar, within one standard deviation, to the values for oleic estolide 2-EH esters. The 2-EH esters have lower PP and CP than the free acids. Without being bound by theory, possible mechanism includes the fact that the free acids can dimerize, agglomerate, etc., due to H-bonding, and promote crystallization/solidification. Lower PP and CP range was clearly observed by iso-estolide 2-EH esters, which can be (without being bound by theory) considered as a plausible influence of the methyl branch in iso-estolide 2-EH esters. Without being bound by theory, it is plausible that the methyl branch can interfere and prevent the hydrocarbon chains from assuming the configurations that favor crystallization and solidification.

Table 10 compares the onset (OT) and peak (PT) oxidation temperatures of oleic vs. iso-oleic estolide 2-EH esters. Without exception, the oleic estolide 2-EH esters displayed slightly higher OT and PT than the corresponding iso-estolide 2-EH esters. In general, OT and PT values for estolide 2-EH esters were higher by 4-17° C. and 3-7° C., respectively, relative to those for iso-estolide 2-EH esters. In general, oleic estolide 2-EH esters displayed slightly higher OT and PT values, but the differences were so small it can be concluded that the two estolides will display similar oxidation stability. As was the case with the free acid estolides, it appears that the presence of random methyl branching did not improve or degrade the oxidation stability of iso-estolides 2-EH esters.

FIG. 9 shows the viscosity and VI results of the branched estolide esters. As obtained, after esterification, there was a decrease of viscosity and increase of VI. 2-EH provided the best VI and lowest viscosity among the branched alcohols. Most of them show slightly lower VI compared to iso-oleic- and oleic-lauric estolide 2-EH esters (159 and 167, respectively), but there wasn't much difference.

FIG. 10 shows the lower temperature properties and oxidation stability of iso-oleic- and oleic-coconut estolide FA and their esters. In general, the higher branching of branched alcohol provided better lower temperature properties. The PP of iso-oleic-coconut estolide 2-EH, 2-PH and 2-BO esters were as low as −45.0° C., −45.0° C., −48.0° C., respectively. Iso-oleic-coconut estolide FAs gave excellent lower temperature properties as well (−39.0° C. of pour point). Esterification modification by 2-EH and 2-BO can slightly improve the oxidation stability of iso-oleic-coconut estolides. Although still not as good as oleic-, the difference was not significant. Surprisingly, iso-oleic- and oleic-coconut FA estolides showed closed and even better oxidation stability than the iso-oleic- and oleic-saturated FA estolides. The OT of iso-oleic-coconut FA esters was 184-198° C. while iso-oleic-saturated FA estolide 2-EH esters was 184-192° C., and oleic-coconut FA esters was 193-204° C. while iso-oleic-saturated FA estolide 2-EH esters was 196-202° C.

Summary: Branched estolide free acids (FAs) and branched estolide C4 to C12 esters were synthesized by the reaction of a series of fatty acids with iso-oleic acid. Similar FAs and C4 to C12 esters were also synthesized by reaction of the same series of fatty acids with oleic acid, using similar (but not identical) reaction conditions. The resulting products displayed comparable TAN, Gardner color, and EN. However, as ester chain length increased lower cold temperatures were recorded. Additionally, better low temperature properties were observed for the branched estolides (FA and ester) verse the standard estolides (FA and ester).

Characterization of the estolide and iso-estolide FAs showed: With some exception, higher kinematic viscosity and viscosity range for iso-estolide 2-EH esters. With some exception, higher VI for estolide 2-EH esters. With minor exception, lower PP and CP for iso-estolide 2-EH esters. With some exception, slightly higher OT and PT for estolide 2-EH esters.

Characterization of the estolide and iso-estolide 2-EH esters showed: With minor exception, higher kinematic viscosity and viscosity range for iso-estolide 2-EH esters. Without exception, higher VI for estolide 2-EH esters. Without minor exceptions, lower PP and CP for iso-estolide 2-EH esters. Without exception, slightly higher OT and PT for estolide 2-EH esters.

It is concluded (based on the PP and CP data in Tables 6 and 9) that iso-oleic acid surprisingly provides iso-estolides with improved cold flow properties relative to those from oleic acid. Improved pour point and cloud point will increase the competitiveness of iso-estolides against petroleum base oils for applications in high volume lubricant formulations such as motor oil, hydraulic, gear oils and many other lubricant products.

It was surprising that we got a better property (i.e., improved cold flow) by substituting iso-oleic acid for oleic acid. Iso-oleic has a very short branch (methyl) that is randomly located along the chain. It was a surprise when we observed major improvements in pour point and cloud point when substituting iso-oleic acid for oleic acid. It is not clear exactly why this happened. Without being bound by theory, one possible explanation is that the estolide ester link primarily occurs on the methyl-substituted carbon resulting in a structure that is very disruptive to crystallization and highly favorable to flow. There may be other reasons as well.

All of the references cited herein, including U.S. patents and U.S. patent application Publications, are incorporated by reference in their entirety. Also incorporated by reference in their entirety are the following references: U.S. Pat. Nos. 6,316,649; 6,018,063; U.S. patent application Ser. No. 16/139,723.

Thus, in view of the above, there is described (in part) the following:

A branched estolide compound of the formula:

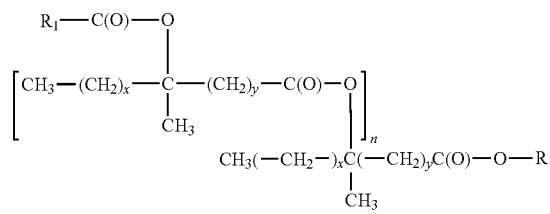

wherein x and y are equal to 1 or greater;
wherein x+y=14;
wherein n is 0, 1, or greater than 1;
wherein R is H (branched estolide free acid or iso-estolide free acid) or wherein R=C1 to C18 straight alcohols or C4 to C12 branched alcohols (branched estolide esters or iso-estolide esters);
wherein $R_1$ is a residual fragment of octanoic, decanoic, lauric, coconut, myristic, palmitic, stearic, oleic, iso-stearic or iso-oleic acids.

The above compound, wherein x=1-12 and wherein y=1-12 but x+y=14.

The above compound, wherein x=4-10 and wherein y=4-10 but x+y=14.

The above compound, wherein n is 0-9.

The above compound, wherein n=1-2.

The above compound, wherein R=H.

The above compound, wherein R=—CH$_2$—CH(CH$_2$CH$_3$)—(CH$_2$)$_3$—CH$_3$ or wherein R=C1 to C18 straight alcohols or C4 to C12 branched alcohols.

The above compound according to claim 1, wherein R$_1$ is C8 to C18 saturated fatty acids, C18:1 unsaturated fatty acids, or C18:1 unsaturated branched fatty acids.

The above compound, wherein said alcohol is 2-ethyl hexanol (the alcohol used herein).

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . . Silence in the specification may be used to establish written description support for a negative limitation. As an example, in Ex parte Lin [No. 2009-0486, at 2, 6 (B.P.A.I. May 7, 2009)] the negative limitation was added by amendment . . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation . . . ."

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Some key chemicals used in our research.

| Name | Purity, % | Source/Location |
| --- | --- | --- |
| Octanoic Acid | 99 | ACROS Organics/Geel, Belgium |
| Decanoic Acid | 96 | ACROS Organics/Geel, Belgium |
| Lauric Acid | 97 | Pfaltz & Bauer, Inc/Waterbury, CT |
| Coconut Acid | >80[a] | ACME HARDESTY/Blue Bell, PA |
| Myristic Acid | 95 | Sigma-Aldrich Co./St. Louis, MO |
| Palmitic Acid | 95 | Sigma-Aldrich Co./St. Louis, MO |
| Stearic Acid | 95 | Sigma-Aldrich Co./St. Louis, MO |
| Oleic Acid | 90 | Sigma-Aldrich Co./St. Louis, MO |
| Iso-Oleic Acid | 78-89 | Synthesized at USDA |
| 2-Methylpropanol (2-MP), C4 | 99 | Sigma-Aldrich Co./St. Louis, MO |
| 2-Ethylbutanol (2-EB), C6 | 98 | Sigma-Aldrich Co./St. Louis, MO |
| 2-Ethylhexanol (2-EH), C8 | 99.5 | Univar/Bedford Park, IL |
| 2-Propylheptanol (2-PH), C10 | 100 | BASF/Florham Park, NJ |
| 2-Butyloctanol (2-BO), C12 | 98.5 | CONDEA VISTA/Austin, TX |
| HClO$_4$ | 70 | Alfa Aesar/Heysham, United Kingdom |
| Potassium Hydroxide | 100 | LabChem/Zelienople, PA |
| Sodium Phosphate Monobasic Monohydrate | 98 | RICCA Co./Arlington, TX |
| Sodium Chloride | 95 | Fischer Chemical/Geel, Belgium |
| Sodium Sulfate Anhydrous | 99 | Fischer Chemical/Geel, Belgium |

[a]Total fatty acids (C6:0 through C18:2) (REF: https://www.acme-hardesty.com/wp-content/uploads/2014/02/Coconut-Fatty-Acid-745-Spec.pdf, Accessed 2019 Nov. 26)

TABLE 2

Estolide Free Acid Synthesis Parameters and Some Characteristics

| FA 2 (mmol) | FA 1 (mmol) | HClO$_4$ Equiv[a] | Temp ° C. | Time h | Yield[b] % | EN[c] | TAN[d] mg KOH/g | Gardner Color[e] |
| --- | --- | --- | --- | --- | --- | --- | --- | --- |
| Octanoic (1866) | Oleic (622) | 0.05 | 60 | 24 | 59.7 | 2.59 | 107.4 | 11 |
| Octanoic (1400) | Iso-oleic (467) | 0.10 | 60 | 48 | 37 | 2.42 | 138.8 | 13 |
| Decanoic (1212) | Oleic (404) | 0.05 | 60 | 24 | 57.4 | 1.89 | 156.6 | 13 |
| Decanoic (1306) | Iso-oleic (435) | 0.10 | 60 | 48 | 24.3 | 2.00 | 129.9 | 15 |
| Lauric (1120) | Oleic (373) | 0.05 | 60 | 24 | 51.8 | 1.63 | 107 | 12 |

TABLE 2-continued

Estolide Free Acid Synthesis Parameters and Some Characteristics

| FA 2 (mmol) | FA 1 (mmol) | HClO$_4$ Equiv[a] | Temp °C. | Time h | Yield[b] % | EN[c] | TAN[d] mg KOH/g | Gardner Color[e] |
|---|---|---|---|---|---|---|---|---|
| Lauric (1213) | Iso-oleic (404) | 0.05 | 60 | 24 | 33.5 | 1.27 | 116 | 12 |
| Coconut (933) | Oleic (311) | 0.04 | 60 | 24 | 65.9 | 1.05 | 109.5 | 14 |
| Coconut (933) | Iso-oleic (311) | 0.05 | 60 | 24 | 56.9 | 1.01 | 119.3 | 17 |
| Coconut (933)[f] | Iso-oleic (311) | 0.05 | 60 | 24 | 35.1 | 1.06 | 131.6 | 10 |
| Myristic (1119) | Oleic (373) | 0.05 | 60 | 24 | 60.8 | 1.35 | 120.6 | 11 |
| Myristic (1213) | Iso-oleic (404) | 0.10 | 60 | 48 | 40 | 1.19 | 131 | 10 |
| Palmitic (1119) | Oleic (373) | 0.05 | 60 | 24 | 58.2 | 1.12 | 96.1 | 10 |
| Palmitic (1119) | Iso-oleic (373) | 0.10 | 60 | 48 | 29.7 | 1.15 | 106.7 | 10 |
| Stearic (933) | Oleic (311) | 0.05 | 70 | 24 | 40.7 | 1.05 | 93.7 | 13 |
| Stearic (1213) | Iso-oleic (404) | 0.10 | 70 | 48 | 28.6 | 1.02 | 129.7 | 14 |
| Oleic (319) | Oleic (319) | 0.04 | 60 | 24 | 74.9 | 1.92 | 61.1 | 8 |
| Iso-oleic (315) | Iso-oleic (315) | 0.10 | 60 | 48 | 50.3 | 1.02 | 103.8 | 12 |

[a]Relative to total moles of fatty acids (FA 1 + FA 2)
[b]Yield is relative to a theoretical maximum of estolide product with estolide number (EN) = 1.
[c]EN, Estolide Number, calculated form Gas Chromatography data as described above.
[d]TAN, Total Acid Number, determined as described above.
[e]Gardner Color obtained as described above.
[f]Values in parenthesis after decolorization with charcoal.

TABLE 3

Estolide 2-Ethylhexyl (2-EH) Ester Synthetic Parameters at 60° C. and Some Characteristics.

| FA 2 (mmol) | FA 1 (mmol) | HClO$_4$ Equiv[a] | 2-EH mmol | Time[b] h | Yield[c] % | EN[d] | TAN[e] mg KOH/g | Gardner Color[f] |
|---|---|---|---|---|---|---|---|---|
| Octanoic (1212) | Oleic (404) | 0.05 | 1940 | 24 + 6 | 36.3 | 2.68 | 1.3 | 12 |
| Octanoic (1400) | Iso-oleic (467) | 0.10 | 2240 | 48 + 6 | 44.9 | 1.69 | 1.9 | 10 |
| Decanoic (1212) | Oleic (404) | 0.05 | 1940 | 24 + 6 | 56.9 | 1.84 | 1.3 | 15 |
| Decanoic (1306) | Iso-oleic (435) | 0.10 | 2089 | 48 + 6 | 35.2 | 1.83 | 2.7 | 10 |
| Lauric (1120) | Oleic (373) | 0.05 | 1792 | 24 + 6 | 66.8 | 1.31 | 1.6 | 11 |
| Lauric (1213) | Iso-oleic (404) | 0.05 | 1940 | 24 + 6 | 32 | 1.34 | 1.4 | 11 |
| Coconut (933) | Oleic (311) | 0.04 | 1493 | 24 + 6 | 66.2 | 1.48 | 0.9 | 13 |
| Coconut (933) | Iso-oleic (311) | 0.05 | 1493 | 24 + 6 | 39.4 | 1.36 | 2.6 | 17 |
| Coconut (933)[g] | Iso-oleic (311) | 0.05 | 1493 | 24 + 6 | 35.0 | 1.27 | 2.5 | 12 |
| Myristic (1119) | Oleic (373) | 0.05 | 1791 | 24 + 6 | 62.8 | 1.01 | 2.1 | 7 |
| Myristic (1213) | Iso-oleic (404) | 0.05 | 1940 | 24 + 6 | 27.9 | 1.31 | 1.7 | 6 |
| Palmitic (1119) | Oleic (373) | 0.05 | 1791 | 24 + 6 | 56 | 1.15 | 1.3 | 7 |
| Palmitic (1119) | Iso-oleic (373) | 0.10 | 1791 | 48 + 6 | 33.9 | 1.01 | 3.2 | 8 |
| Stearic (933)[h] | Oleic (311) | 0.05 | 1493 | 24 + 6 | 47.6 | 1.03 | 0.9 | 12 |
| Stearic (1213)[h] | Iso-oleic (404) | 0.10 | 1940 | 48 + 6 | 24.1 | 1.01 | 1.8 | 11 |
| Oleic (319) | Oleic (319) | 0.04 | 766 | 24 + 6 | 75.3 | 1.96 | 1.5 | 7 |
| Iso-oleic (315) | Iso-oleic (315) | 0.1 | 756 | 48 + 6 | 46.3 | 1.54 | 2.3 | 9 |

[a]Relative to total moles of fatty acids (FA 1 + FA 2)
[b]Time for Estolide free acid synthesis plus Estolide 2-EH ester synthesis
[c]Yield is relative to a theoretical maximum of estolide product with estolide number (EN) = 1.
[d]EN, Estolide Number, calculated form gas chromatography as described above.
[e]TAN, Total Acid Number, determined as described above.
[f]Gardner Color obtained as described above.
[g]Yield and other values in parenthesis after decolorization with charcoal.
[h]Synthesis done at 70° C. not 60° C.

TABLE 4

Synthesis of iso-oleic- and oleic-coconut estolide free acids and esters.

| FA[a] 2 (mmol) | FA[a] 1 (mmol) | HClO$_4$ (equiv.) | Alcohol (mmol) | Temp. (° C.) | Time (h) | Yield[b,c] (%) |
|---|---|---|---|---|---|---|
| Coconut (933) | Iso-oleic (311) | 0.05 | None | 60 | 24 | 57/35 |
| Coconut (933) | Iso-oleic (311) | 0.1 | 2MP (1493) | 60 | 48 + 6 | 31/26 |
| Coconut (933) | Iso-oleic (311) | 0.1 | 2EB (1493) | 60 | 48 + 6 | 45/38 |
| Coconut (933) | Iso-oleic (311) | 0.05 | 2EH (1493) | 60 | 24 + 6 | 39/35 |
| Coconut (933) | Iso-oleic (311) | 0.1 | 2PH (1493) | 60 | 48 + 6 | 46/40 |
| Coconut (933) | Iso-oleic (311) | 0.1 | 2BO (1493) | 60 | 48 + 6 | 43/36 |
| Coconut (933) | Oleic (311) | 0.04 | None | 60 | 24 | 66 |
| Coconut (933) | Oleic (311) | 0.05 | 2MP (1493) | 60 | 24 + 6 | 41 |
| Coconut (933) | Oleic (311) | 0.05 | 2EB (1493) | 60 | 24 + 6 | 66 |
| Coconut (933) | Oleic (311) | 0.04 | 2EH (1493) | 60 | 24 + 6 | 66 |
| Coconut (933) | Oleic (311) | 0.05 | 2PH (1493) | 60 | 24 + 6 | 61 |
| Coconut (933) | Oleic (311) | 0.05 | 2BO (1493) | 60 | 24 + 6 | 62 |

[a]FA—Fatty acid
[b]Yield (bracketed) is relative to a theoretical maximum of estolide product with estolide number EN = 1
[c]x/y: before charcoal cleaning/after charcoal cleaning

TABLE 5

Kinematic viscosity and VI of Oleic vs. iso-Oleic Estolide Free Acids

| | kVisc @ 40, cSt | | kVisc @ 100 cSt | | VI | |
|---|---|---|---|---|---|---|
| FA 2 | FA 1 = Oleic Estolide | FA 1 = iso-Oleic Branched Estolide | FA 1 = Oleic Estolide | FA 1 = iso-Oleic Branched Estolide | FA 1 = Oleic Estolide | FA 1 = iso-Oleic Branched Estolide |
| Octanoic | 149.53 ± 0.04 | 315.81 ± 0.05 | 17.99 ± 0.00 | 27.75 ± 0.02 | 133.7 ± 0.0 | 117.8 ± 0.1 |
| Decanoic | 139.42 ± 0.08 | 892.03 ± 0.50 | 16.97 ± 0.00 | 55.51 ± 0.00 | 132.1 ± 0.7 | 116.4 ± 0.1 |
| Lauric | 167.15 ± 0.06 | 165.52 ± 0.04 | 19.46 ± 0.03 | 18.42 ± 0.03 | 133.5 ± 0.2 | 124.5 ± 0.3 |
| Coco | 122.42 ± 0.02 | 72.03 ± 0.08 | 15.82 ± 0.00 | 10.79 ± 0.01 | 136.7 ± 0.0 | 138.4 ± 0.1 |
| Myristic | 149.39 ± 0.18 | 198.00 ± 0.10 | 18.21 ± 0.00 | 20.77 ± 0.00 | 136.1 ± 0.2 | 123.5 ± 0.1 |
| Palmitic | 141.51 ± 0.04 | 266.20 ± 0.19 | 17.62 ± 0.00 | 26.08 ± 0.01 | 137.3 ± 0.0 | 127.1 ± 0.1 |
| Stearic | 159.58 ± 0.34 | 610.54 ± 1.68 | 19.25 ± 0.01 | 44.30 ± 0.11 | 137.3 ± 0.4 | 120.20 ± 0.2 |
| Oleic | 314.81 ± 0.33 | | 32.63 ± 0.02 | | 144.7 ± 0.0 | |
| iso-Oleic | | 471.66 ± 0.95 | | 37.73 ± 0.05 | | 122.6 ± 0.1 |

TABLE 6

Pour Point (PP) and Cloud Point (CP) of Oleic vs. iso-Oleic Estolide Free Acids

| | Pour Point, ° C. | | Cloud Point, ° C. | |
|---|---|---|---|---|
| FA 2 | FA 1 = Oleic Estolide | FA 1 = iso-Oleic Branched Estolide | FA 1 = Oleic Estolide | FA 1 = iso-Oleic Branched Estolide |
| Octanoic | −46.7 ± 4.2 | −38.0 ± 1.7 | −39.7 ± 0.6 | −34.8 ± 3.6 |
| Decanoic | −34.5 ± 1.7 | −26.0 ± 1.7 | −34.0 ± 0.0 | −63.7 ± 2.7 |
| Lauric | −32.0 ± 1.7 | −38.0 ± 1.7 | −29.2 ± 0.4 | −32.2 ± 0.4 |
| Coco | −12.0 ± 0.0 | −39.0 ± 0.0 | −4.3 ± 0.5 | −17.8 ± 0.5 |
| Myristic | −19.8 ± 3.5 | −26.3 ± 1.5 | −16.0 ± 0.0 | −18.7 ± 1.2 |
| Palmitic | −9.0 ± 0.0 | −9 ± 0.0 | −7.0 ± 0.0 | −8 ± 0.0 |
| Stearic | 6.0 ± 0.0 | −3 ± 0.0 | 10.3 ± 2.1 | 0.0 ± 0.0 |
| Oleic | −30.0 ± 0.0 | | −32.3 ± 1.2 | −43.7 ± 0.7 |
| iso-oleic | | −32 ± 1.7 | | −43.5 ± 0.7 |

TABLE 7

Onset (OT) and Peak (PT) oxidation temperatures of Oleic vs. iso-Oleic Estolide Free Acids

| | PDSC-OT, °C. | | PDSC-PT, °C. | |
| --- | --- | --- | --- | --- |
| FA 2 | FA 1 = Oleic Estolide | FA 1 = iso-Oleic Branched Estolide | FA 1 = Oleic Estolide | FA 1 = iso-Oleic Branched Estolide |
| Octanoic | 169.11 ± 0.59 | 160.87 ± 1.68 | 189.86 ± 1.21 | 181.77 ± 0.64 |
| Decanoic | 172.93 ± 0.12 | 155.86 ± 2.27 | 191.66 ± 0.23 | 179.02 ± 1.27 |
| Lauric | 169.57 ± 0.39 | 162.87 ± 0.38 | 190.4 ± 0.13 | 180.29 ± 1.21 |
| Coco | 204.22 ± 0.96 | 192.87 ± 0.29 | 222.40 ± 0.23 | 213.47 ± 0.82 |
| Myristic | 173.65 ± 0.10 | 166.47 ± 1.46 | 191.99 ± 0.45 | 187.17 ± 0.73 |
| Palmitic | 178.78 ± 1.04 | 186.46 ± 0.34 | 195.54 ± 0.23 | 214.36 ± 0.08 |
| Stearic | 178.66 ± 0.87 | 180.04 ± 6.53 | 195.68 ± 0.04 | 221.96 ± 3.9 |
| Oleic | 192.82 ± 0.38 | | 216.26 ± 0.77 | |
| iso-oleic | | 171.29 ± 2.96 | | 212.74 ± 4.55 |

TABLE 8

Kinematic viscosity and VI of Oleic vs. iso-Oleic Estolide 2-EH Esters

| | kVisc @ 40, cSt | | kVisc @ 100 cSt | | VI | |
| --- | --- | --- | --- | --- | --- | --- |
| FA 2 | FA 1 = Oleic Estolide | FA 1 = iso-Oleic Branched Estolide | FA 1 = Oleic Estolide | FA 1 = iso-Oleic Branched Estolide | FA 1 = Oleic Estolide | FA 1 = iso-Oleic branched Estolide |
| Octanoic | 46.18 ± 0.00 | 42.03 ± 0.01 | 17.99 ± 0.00 | 7.74 ± 0.00 | 164.3 ± 0.1 | 155.8 ± 0.1 |
| Decanoic | 36.17 ± 0.02 | 48.34 ± 0.02 | 16.97 ± 0.00 | 8.52 ± 0.00 | 165.2 ± 0.1 | 154.0 ± 0.1 |
| Lauric | 31.96 ± 0.01 | 41.11 ± 0.02 | 19.46 ± 0.03 | 7.69 ± 0.01 | 167.6 ± 0.1 | 158.75 ± 0.4 |
| Coco | 42.74 ± 0.02 | 42.02 ± 0.01 | 15.82 ± 0.00 | 7.91 ± 0.00 | 167.2 ± 0.3 | 162.3 ± 0.1 |
| Myristic | 33.78 ± 0.03 | 41.73 ± 0.02 | 18.21 ± 0.00 | 7.82 ± 0.01 | 171.2 ± 0.5 | 160.5 ± 0.1 |
| Palmitic | 42.58 ± 0.02 | 54.12 ± 0.02 | 17.62 ± 0.00 | 9.40 ± 0.01 | 170.0 ± 0.1 | 157.8 ± 0.1 |
| Stearic | 44.73 ± 0.09 | 64.49 ± 0.01 | 19.25 ± 0.01 | 10.60 ± 0.00 | 172.5 ± 0.4 | 154.0 ± 0.0 |
| Oleic | 94.31 ± 0.13 | | 32.63 ± 0.02 | | 168.4 ± 0.1 | |
| iso-Oleic | | 86.76 ± 0.02 | | 13.15 ± 0.01 | | 152.0 ± 0.1 |

TABLE 9

Pour Point and Cloud Point of Oleic vs. iso-Oleic Estolide 2-EH Esters

| | Pour Point, °C. | | Cloud Point, °C. | |
| --- | --- | --- | --- | --- |
| FA 2 | FA 1 = Oleic Estolide | FA 1 = iso-Oleic Branched Estolide | FA 1 = Oleic Estolide | FA 1 = iso-Oleic Branched Estolide |
| Octanoic | −51.0 ± 0.0 | <−60 | −23.0 ± 2.6 | −22 ± 1.0 |
| Decanoic | −42.0 ± 0.0 | <−60 | −38.3 ± 4.2 | −42 ± 0.9 |
| Lauric | −36.0 ± 0.0 | −48.0 ± 2.4 | −29 ± 0.0 | −25.0 ± 4.0 |
| Coco | −33.0 ± 0.0 | −45.0 ± 0.0 | −13.0 ± 2.4 | −22.3 ± 1.2 |
| Myristic | −27.0 ± 0.0 | −33.0 ± 0.0 | −25.0 ± 0.0 | −29.3 ± 2.1 |
| Palmitic | −18.0 ± 0.0 | −24 ± 0.0 | −15.0 ± 0.0 | −18.3 ± 0.6 |
| Stearic | −12.0 ± 0.0 | −20 ± 1.7 | −9.3 ± 0.6 | −10.0 ± 0.0 |
| Oleic | −40.0 ± 3.5 | | −37.7 ± 0.6 | |
| iso-oleic | | −53.0 ± 1.7 | | −32.5 ± 10.6 |

TABLE 10

Onset (OT) and Peak (PT) Oxidation Temperatures
of Oleic vs. iso-Oleic Estolide 2-EH Esters

| | FA 2 | | | |
|---|---|---|---|---|
| | PDSC-OT, ° C. | | PDSC-PT, ° C. | |
| FA 2 | FA 1 = Oleic Estolide | FA 1 = Iso-Oleic Branched Estolide | FA 1 = Oleic Estolide | FA 1 = iso-Oleic Branched Estolide |
| Octanoic | 198.78 ± 0.52 | 184.41 ± 0.93 | 221.65 ± 0.01 | 214.07 ± 1.07 |
| Decanoic | 199.64 ± 0.19 | 189.71 ± 1.72 | 221.43 ± 0.29 | 217.22 ± 0.74 |
| Lauric | 198.70 ± 0.95 | 188.39 ± 3.11 | 220.10 ± 0.29 | 217.60 ± 1.20 |
| Coco | 200.36 ± 0.69 | 196.21 ± 0.66 | 223.21 ± 1.01 | 219.18 ± 0.16 |
| Myristic | 196.37 ± 0.78 | 192.05 ± 3.82 | 221.45 ± 1.29 | 218.04 ± 0.81 |
| Palmitic | 200.11 ± 0.74 | 188.32 ± 1.77 | 220.65 ± 0.06 | 215.52 ± 0.06 |
| Stearic | 202.24 ± 0.03 | 185.42 ± 0.39 | 222.07 ± 0.15 | 214.89 ± 0.38 |
| Oleic | 191.37 ± 0.28 | | 220.16 ± 0.59 | |
| iso-oleic | | 179.26 ± 0.58 | | 214.94 ± 0.61 |

We claim:

1. A branched estolide compound of the formula:

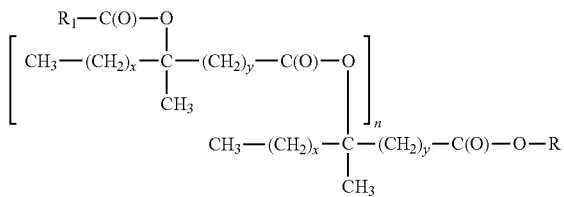

wherein x and y are equal to 1 or greater;
wherein x+y=14;
wherein n is 0, 1, or greater than 1;
wherein R is H, —CH$_2$—CH(CH$_2$CH$_3$)—(CH$_2$)$_3$—CH$_3$, or C1 to C18 straight alcohols, or C4 to C12 branched alcohols;
wherein R$_1$ is a residual fragment of octanoic, decanoic, lauric, coconut, myristic, palmitic, stearic, oleic, iso-stearic or iso-oleic acids; and
wherein the branched estolide has a lower oxidative stability than a non-branched estolide.

2. The compound according to claim 1, wherein x=1-12 and wherein y=1-12 but x+y=14.

3. The compound according to claim 1, wherein x=4-10 and wherein y=4-10 but x+y=14.

4. The compound according to claim 1, wherein n is 0-9.

5. The compound according to claim 1, wherein n=1-2.

6. The compound according to claim 1, wherein R=H.

7. The compound according to claim 1, wherein R=—CH$_2$—CH(CH$_2$CH$_3$)—(CH$_2$)$_3$—CH$_3$.

8. The compound according to claim 1, wherein R$_1$ is C8 to C18 saturated fatty acids, C18:1 unsaturated fatty acids, or C18:1 unsaturated branched fatty acids.

9. The compound according to claim 1, wherein said alcohol is 2-ethyl hexanol.

* * * * *